(12) United States Patent
Dosaka et al.

(10) Patent No.: US 7,570,362 B2
(45) Date of Patent: Aug. 4, 2009

(54) OPTICAL MEASUREMENT APPARATUS UTILIZING TOTAL REFLECTION

(75) Inventors: Shinichi Dosaka, Sagamihara (JP); Yoshimasa Suzuki, Kawasaki (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 12/229,128

(22) Filed: Aug. 19, 2008

(65) Prior Publication Data

US 2009/0086211 A1    Apr. 2, 2009

(30) Foreign Application Priority Data

Sep. 28, 2007   (JP)   ............... 2007-255041
Nov. 28, 2007   (JP)   ............... 2007-307055

(51) Int. Cl.
*G01N 21/55* (2006.01)
*G01N 21/41* (2006.01)

(52) U.S. Cl. ....................... 356/445; 356/128
(58) Field of Classification Search ................. 356/445, 356/128
See application file for complete search history.

(56) References Cited

U.S. PATENT DOCUMENTS

| | | | |
|---|---|---|---|
| 5,491,556 A * | 2/1996 | Stewart et al. | 356/445 |
| 6,088,115 A * | 7/2000 | Ohsaki et al. | 356/445 |
| 6,215,549 B1 * | 4/2001 | Suzuki et al. | 356/338 |
| 2006/0001884 A1 | 1/2006 | Tani et al. | |

FOREIGN PATENT DOCUMENTS

| | | |
|---|---|---|
| JP | 10-48130 | 2/1998 |
| JP | 2005-337940 | 12/2005 |
| JP | 2006-17648 | 1/2006 |

* cited by examiner

*Primary Examiner*—Roy Punnoose
(74) *Attorney, Agent, or Firm*—Kenyon & Kenyon LLP

(57) ABSTRACT

In optical measurement utilizing total reflection, various types of measurement are selectively performed. The invention provides an optical measurement apparatus using total reflection, including a light source, a measurement optical system, and a light detector. The measurement optical system is an infinity-corrected positive lens formed of an optical member having a planar surface orthogonal to an optical axis of the measurement optical system at a front focal position. One side of the optical axis of the measurement optical system is used as a projection optical system for radiating measurement light onto a specimen, and another side is used as a photometric optical system for acquiring reflected light from the specimen. The light source is disposed at an entrance pupil position on the projection optical system side or at a position conjugate to the entrance pupil position and moves in an entrance pupil plane or in a plane conjugate to the entrance pupil position, along a straight line orthogonal to the optical axis, while a distance from the optical axis is detected. The light detector is disposed at an exit pupil position on the photometric optical system side or at a position conjugate to the exit pupil position. The optical-measurement apparatus comprises a light-source changing unit configured to change the position or shape of the light source.

13 Claims, 13 Drawing Sheets

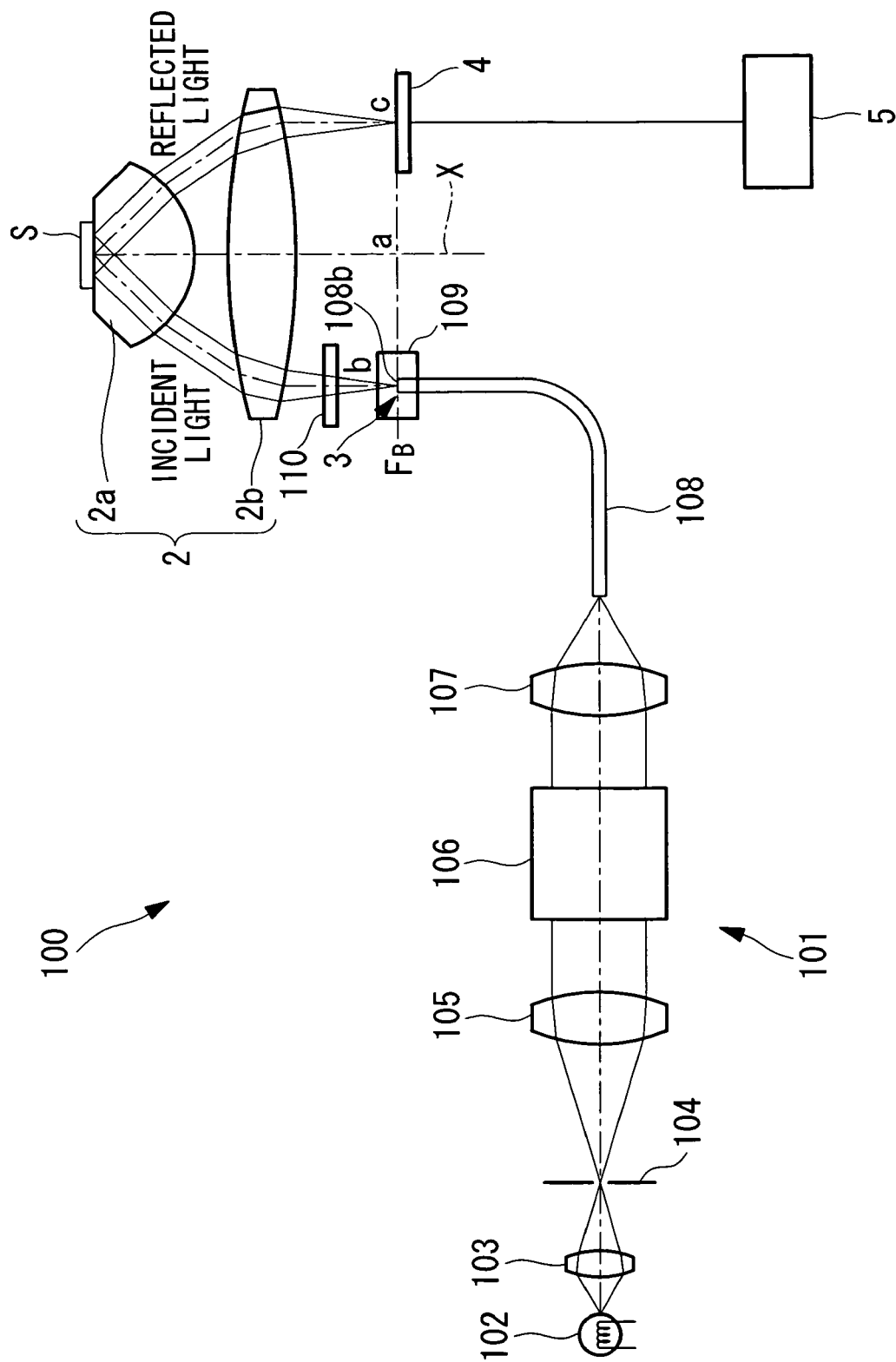

OPTICAL MEASUREMENT APPARATUS UTILIZING TOTAL REFLECTION

BACKGROUND OF THE INVENTION

1. Field of the Invention

The present invention relates to optical measurement apparatuses for measurement of refractive index, plasmon resonance etc. by using total reflection.

This application is based on Japanese Patent Applications, No. 2007-255041 and No. 2007-307055, the contents of which are incorporated herein by reference.

2. Description of Related Art

Microscopes utilizing total reflection are known in the related art (for example, see Japanese Unexamined Patent Application, Publication No. 2005-337940). In this microscope, a collimated beam is made incident on an objective lens for total-reflection fluorescence observation and is converged at the focal position thereof. This microscope can perform refractive-index measurement etc. in a minute region of an object to be observed.

BRIEF SUMMARY OF THE INVENTION

The present invention provides the following solutions.

A first aspect of the present invention is an optical measurement apparatus using total reflection, including a light source, a measurement optical system, and a light detector, wherein the measurement optical system is an infinity-corrected positive lens formed of an optical member having a planar surface orthogonal to an optical axis of the measurement optical system at a front focal position; wherein one side of the optical axis of the measurement optical system is used as a projection optical system configured to radiate measurement light onto a specimen, and another side is used as a photometric optical system configured to acquire reflected light from the specimen; wherein the light source is disposed at an entrance pupil position on the projection optical system side or at a position conjugate to the entrance pupil position and moves in an entrance pupil plane or in a plane conjugate to the entrance pupil position, along a straight line orthogonal to the optical axis, while a distance from the optical axis is detected; and wherein the light detector is disposed at an exit pupil position on the photometric optical system side or at a position conjugate to the exit pupil position; the optical-measurement apparatus comprising a light-source changing unit configured to change the position or shape of the light source.

In the aspect of the invention described above, the light source may be a point light source formed by converging a collimated light beam with a focusing lens, and may be inserted in and removed from the optical axis of the projection optical system by the light-source changing unit.

In the aspect of the invention described above, the light source may be a point light source formed by guiding light with a single-mode fiber, and may be inserted in and removed from the optical axis of the projection optical system by the light-source changing unit.

In the aspect of the invention described above, the light source may be changed to a line light source orthogonal to the optical axis, which is converged by a cylindrical lens constituting the light-source changing unit.

In the aspect of the invention described above, the light source may be changed to a planar light source formed as a collimated beam parallel to the optical axis by an aperture member constituting the light-source changing unit.

In the configuration described above, the light-source changing unit may include an aperture member disposed at the entrance pupil position or at a position conjugate to the entrance pupil position.

In the aspect of the invention described above, the light-source changing unit may include a positive lens disposed in such a manner as to be insertable in and removable from the collimated beam and configured to form a point image at the entrance pupil position.

Furthermore, the aspect of the invention described above may further include a white light source and a spectral device, disposed at entrance and exit sides of the light source, and the light source may be a guided with a multimode fiber.

In the aspect of the invention described above, the optical member may comprise two optical elements, including a parallel flat plate disposed at the flat surface side, and a thin layer of liquid interposed between the two optical elements, and the parallel flat plate is disposed so as to be movable in a direction along the surface of the other optical element.

In the configuration described above, the light-source changing unit may move the aperture member in a direction orthogonal to the optical axis.

In the aspect of the invention described above, the parallel flat plate may be capable of moving in a direction orthogonal to the optical axis, and the optical measurement apparatus may further comprise a movement-amount measuring device configured to measure an amount of movement of the parallel flat plate.

The configuration described above, may further comprise a one-axis or two-axis moving stage configured to move the parallel flat plate, wherein the movement-amount measuring device may be a micrometer.

BRIEF DESCRIPTION OF THE SEVERAL VIEWS OF THE DRAWINGS

FIG. 16 is a diagram showing the overall configuration of an optical measurement apparatus according to a seventh embodiment of the present invention.

DETAILED DESCRIPTION OF THE INVENTION

An optical measurement apparatus according to a first embodiment of the present invention will be described in detail below with reference to FIG. 1 and FIGS. 2A to 2C.

Figure 1:
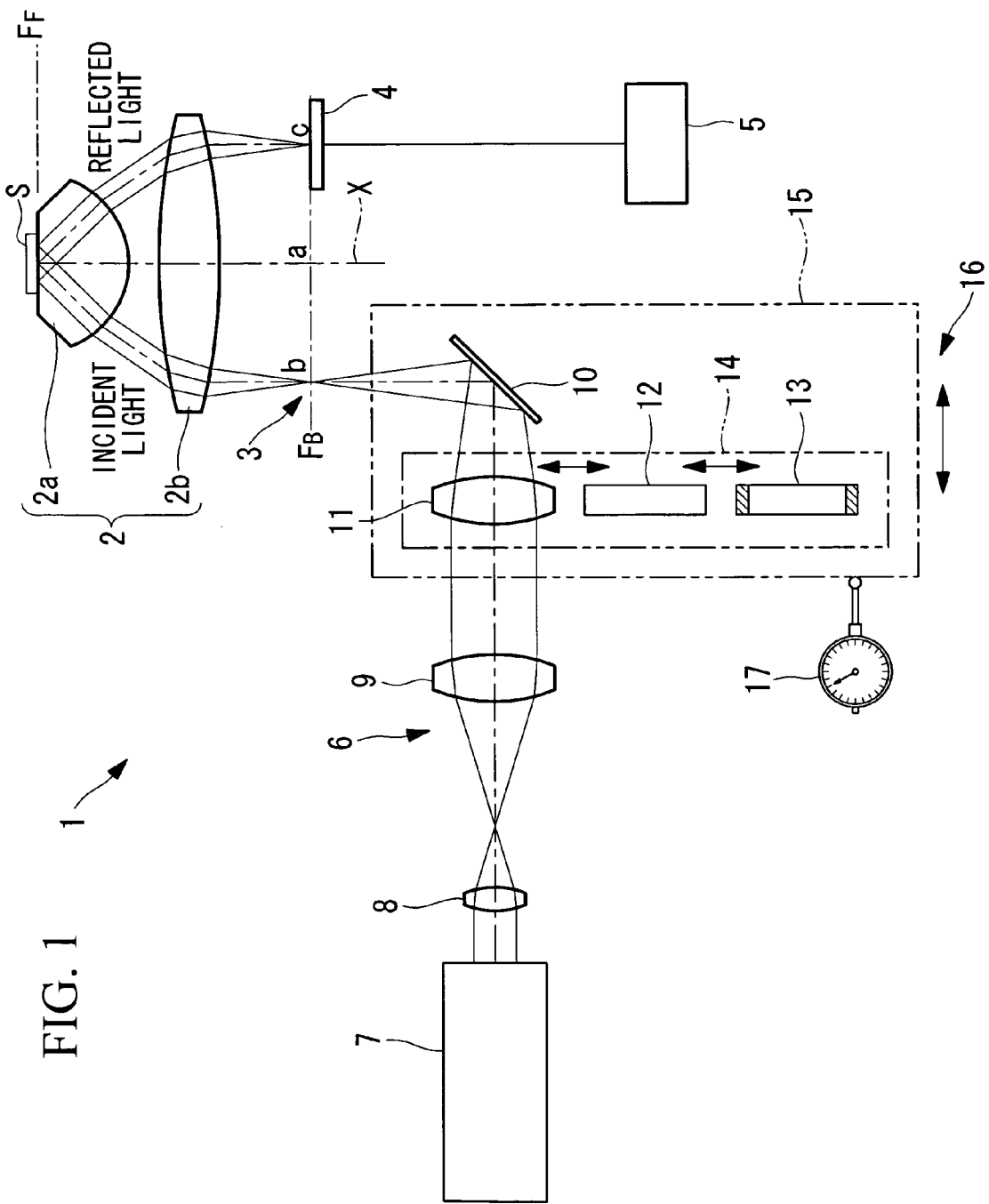
FIG. 1 is a diagram showing the overall configuration of an optical measurement apparatus according to a first embodiment of the present invention.

As shown in FIG. 1, the optical measurement apparatus according to this embodiment, which is a refractive-index measuring device 1, includes an optical system 2, a light source 3, and a light detector 4.

Figure 2A:
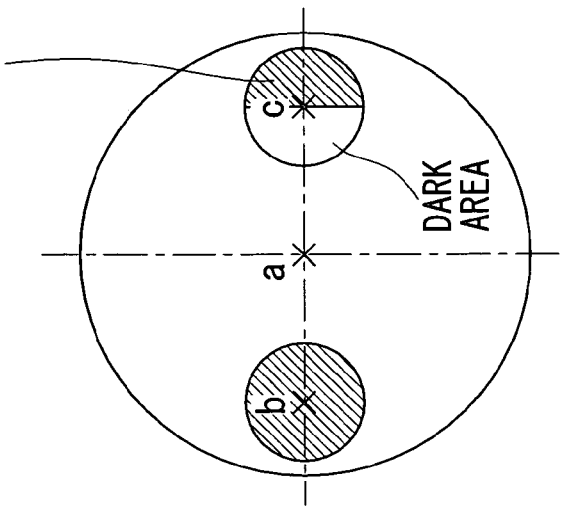
FIG. 2A is a view of a pupil plane of an optical system in the optical measurement apparatus in FIG. 1, showing a case where a cylindrical lens is inserted into the light path.
Figure 2B:
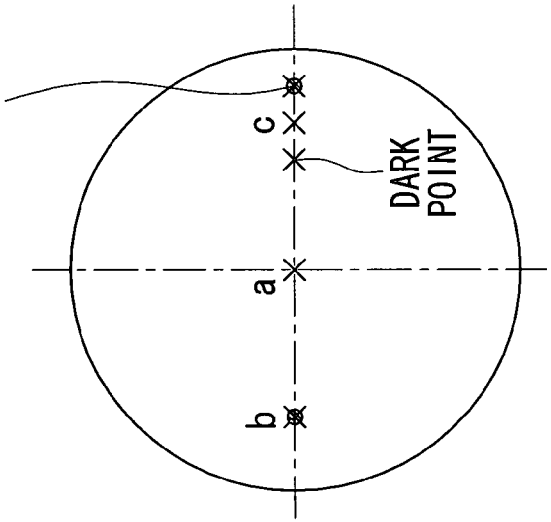
FIG. 2B is a view of the pupil plane of the optical system in the optical measurement apparatus in FIG. 1, showing a case where a focusing lens is inserted into the light path.
Figure 2C:
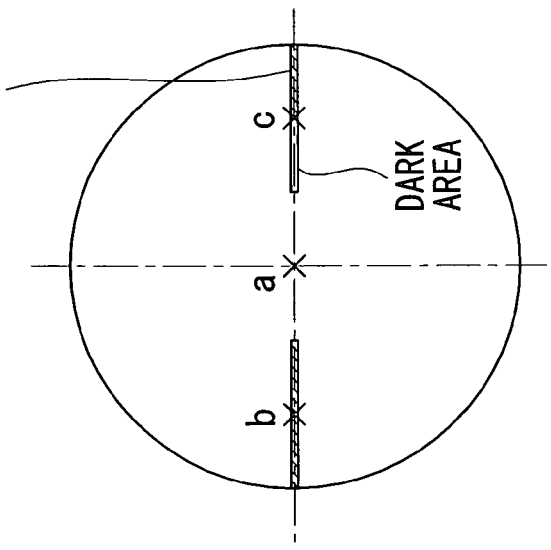
FIG. 2C is a view of the pupil plane of the optical system in the optical measurement apparatus in FIG. 1, showing a case where an aperture is inserted into the light path.

FIG. 1 is a diagram showing, in outline, the configuration of the refractive-index measuring device 1 according to this embodiment, and FIGS. 2A to 2C are views of the pupil plane.

The optical system 2 includes two optical elements (optical members) 2a and 2b. The optical element 2a is a lens having a plano-convex shape; one surface thereof is flat and is disposed at a front focal position $F_F$ of the optical system 2, and the other surface thereof is curved. The flat surface is used as a mounting surface for mounting a specimen S. If the specimen S is a section of biological tissue, the specimen S is directly mounted on the flat surface, but if the specimen S is glass etc., immersion oil is placed therebetween. It is preferable that the refractive index of the immersion oil be between the refractive indexes of the specimen S and the optical element 2a, but it is acceptable if total reflection does not occur between the immersion oil and the optical element 2a at a small angle of incidence, due to total reflection at the specimen S. The immersion oil is any medium used in microscopes or a liquid such as methylene iodide. The other optical element 2b is a biconvex lens in which both surfaces are curved. Also, the optical elements 2a and 2b are separate elements (non-cemented lenses).

The structure of the optical system 2 as described here is for simplifying the explanation thereof; the actual number of optical elements may be two or more, and it need not be constructed of separate elements. One necessary condition, however, is that the front surface of the optical element 2a should be a flat surface orthogonal to the optical axis and containing the front focal point; in other words, the front surface should be coincident with the front focal plane.

In this embodiment, the relative distance between the optical element 2a and the specimen S does not change. Additionally, the optical element 2b does not move either. Therefore, the relative distance between the optical system 2 and the specimen S does not change, and the relative distance between the specimen S and the position of the entrance pupil formed by the optical elements 2a and 2b does not change either.

Accordingly, in the measurement procedure, the specimen is simply placed on the mounting stage and is irradiated with measurement light; it is not necessary to perform focusing, thus reducing measurement errors and simplifying the procedure.

The light source 3 is disposed on one side of an optical axis X of the optical system 2. This light source 3 is formed at a position indicated by reference symbol $F_B$ in FIG. 1, in other words, at the back focal plane $F_B$ of the optical system 2, and can be moved while detecting the distance from the optical axis. The back focal plane $F_B$ of the optical system 2 is also the entrance pupil position (exit pupil position) of the optical system 2.

It is generally considered that the range of movement of the light source 3 must fill the entrance pupil; in practice, however, from the formula for refractive index, it may have a size corresponding to an angle of incidence of 40° to 75° at the specimen S. When a point light source is formed in the pupil as the light source 3, the point light source (light source) 3 must move in this range while the position thereof is detected. When a planar light source or a line light source is formed using a collimated beam or a cylindrical lens, the point light source 3 need not move, so long as it has a diameter or length that fills this range. However, because the beam emitted from a laser light source has an intensity distribution, in general it is preferable to widen the beam with a beam expander lens and to use only the flat portion near the center of the intensity distribution as the incident light. In this case, because the incident light does not fill this range, it is better to move the light source.

In this embodiment, as shown in FIG. 1, a light source changing unit 15 including a mirror 10 and a switching mechanism (slider) 14, which will be described later, is moved as single unit by a moving mechanism (light source changing unit) 16; a focusing lens (positive lens) 11, a cylindrical lens 12, and an aperture (aperture member) 13 are fixed to the switching mechanism (slider) 14; and each optical element is inserted in and removed from the optical axis of the laser light source 7. Reference numeral 17 in the drawing is a length-measuring device for measuring the amount of motion of the moving mechanism 16.

A coherent light source or an incoherent light source is used as the light source 3. Coherent light sources include laser light sources. Incoherent light sources include light sources having broad spectral characteristics (white light sources), including halogen lamps, xenon lamps, and LEDs. A polarizing element may be disposed between the mirror 10 and the optical system 2.

The light detector 4 is disposed on the other side of the optical axis X of the optical system 2. The position of this light detector 4 is the back focal plane position $F_B$ of the optical system 2. The light detector 4 may be a photomultiplier, a photodetector, a line sensor, an image sensor, a position sensor etc.

The light detector 4 should be large enough to fill the pupil of a photometric optical system; in practice, its size should correspond to an angle of incidence of 40 to 70 degrees at the specimen. However, because a large light detector 4 is expensive and has poor precision, it is preferable to select a light detector 4 with a small photoreceptor surface and superior precision, and to move it with opposite synchronization to the movement of the light source 3.

The refractive-index measuring device 1 may include a calculating unit 5. The calculating unit 5 is connected to the light detector 4. The calculating unit 5 calculates the refractive index of the specimen S on the basis of the output signal from the light detector 4.

For example, in FIG. 1, the angle of incidence θ at the specimen can be calculated from the focal length of the measurement optical system and the distance between point a on the optical axis and point b at the light source 3, and when the angle of incidence θ reaches the total reflection angle, total reflection light is focused at point c. Therefore, when the light source at b is moved from point a towards the edge of the pupil, and the position of the light source at b, where the light detector 4 detects the total reflection light, is measured, the refractive index can be measured.

The refractive-index measuring device 1 further includes a light-source-side optical system 6 forming the light source 3 at the back focal plane $F_B$ of the optical system 2. The light-source-side optical system 6 includes a laser light source 7, a focusing lens 8, a collimator lens 9, and the mirror 10.

The light-source-side optical system 6 further includes the focusing lens 11, the cylindrical lens 12, and the aperture member 13. Also, the refractive-index measuring device 1 includes the switching mechanism (slider) 14 for positioning any one of the focusing lens 11, the cylindrical lens 12, and the aperture member 13 in the light path between the collimator lens 9 and the mirror 10. The focusing lens 11, the cylindrical lens 12, the aperture member 13, and the switching mechanism 14 constitute the light source changing unit 15.

When the cylindrical lens 12 is disposed in the light path, as shown in FIG. 2A, a line-shaped beam is formed at the pupil plane (back focal position) $F_B$. The illumination light radiated on the specimen S is incident on the specimen as a line-shaped beam orthogonal to the line-shaped light source formed at the pupil, and a portion of the line-shaped beam having an angle of incidence equal to or greater than the total reflection angle is formed on the light detector 4. Therefore, a line sensor should be provided as the light detector 4, and it should be determined at which pixel the light intensity rises. The direction of the line-shaped beam on the pupil plane when the cylindrical lens is rotated by 90 degrees may be orthogonal to the direction of the line-shaped beam described above. In this case, the pixel where the received light intensity is maximized should be found and the intensity is measured.

When the focusing lens 11 is disposed in the light path, as shown in FIG. 2B, a light spot is formed at the pupil plane $F_B$. When point b corresponds to the total reflection angle or above, point c is a bright point; below the total reflection angle, it is a dark point. The illumination light radiated onto the specimen S is a collimated beam (circular). When the aperture member 13 is disposed in the light path, as shown in FIG. 2C, an apertured planar light source is formed at the pupil plane $F_B$. The illumination light radiated onto the specimen S is spot-shaped. In this case, an image sensor is provided as the light detector 4. When total reflection occurs, the aperture image becomes darker closer to the optical axis a, and the edges become brighter, forming a ring. The refractive index is measured from the position of this ring. Basically, in this measurement, if the light detector 4 is an image sensor, it can be used in all cases.

With the refractive-index measuring device 1 according to this embodiment, the shape of the light source 3 formed at the pupil plane of the optical system 2 can be changed by operating the light-source changing unit 15, and the shape of the illumination light radiated onto the specimen S can thus be changed. This configuration affords some advantages: when measuring the refractive index of a minute area on the specimen S, it is possible to perform measurement with a converging beam by inserting the aperture member 13; when measuring the average refractive index of a surface of the specimen S, it is possible to perform measurement with a collimated beam by inserting the focusing lens 11; and when measuring the refractive index of a single cross-sectional plane of the specimen, it is possible to perform measurement using a line-shaped converging beam.

Next, an optical measurement apparatus according to a second embodiment of the present invention will be described below with reference to FIGS. 3 to 5B.

In the description of this embodiment, parts having the same configuration as those in the optical measurement apparatus according to the first embodiment described above are assigned the same reference numerals, and a description thereof is omitted.

The optical measurement apparatus according to this embodiment is also a refractive-index measuring device 20.

Figure 3:
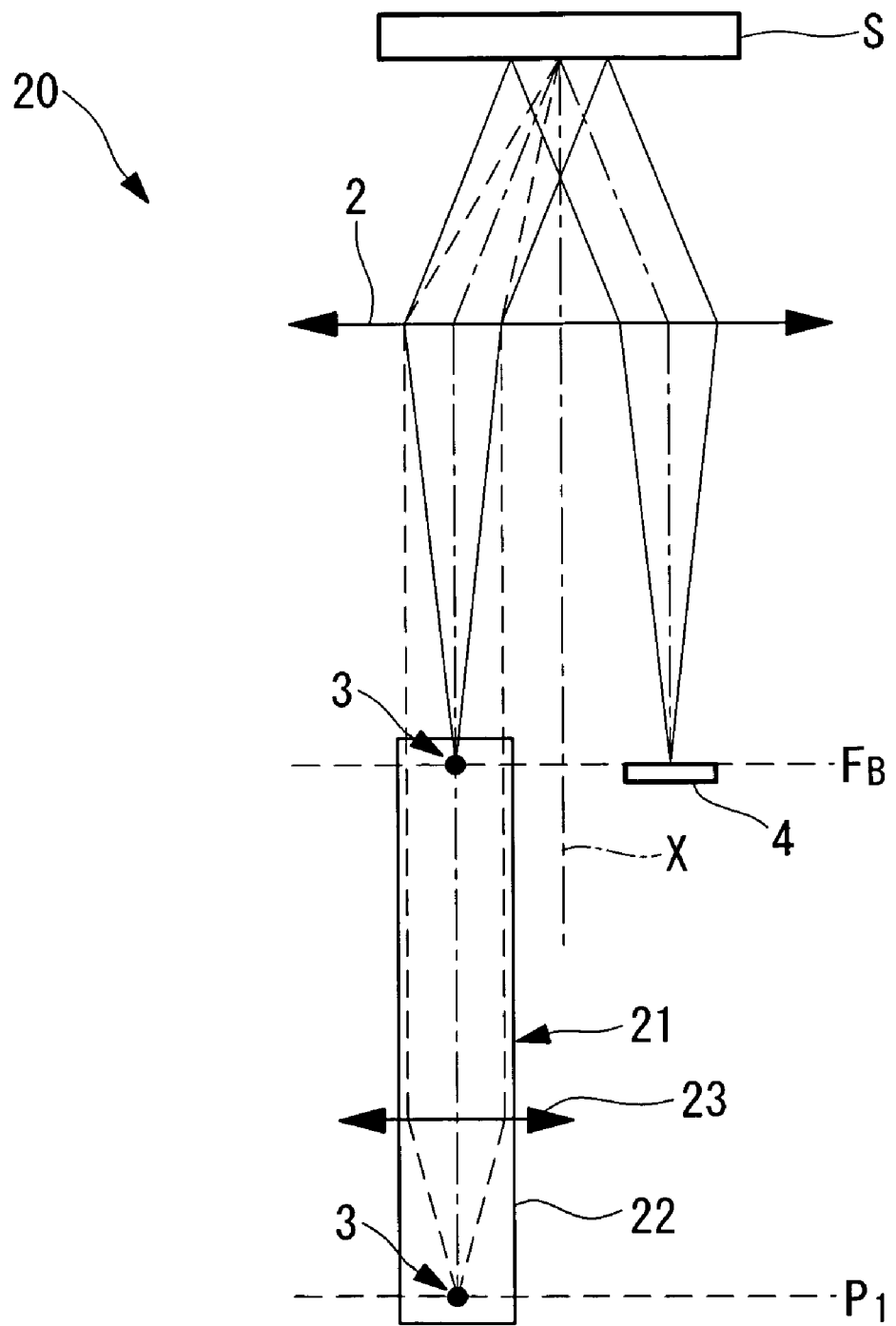
FIG. 3 is a diagram showing the overall configuration of an optical measurement apparatus according to a second embodiment of the present invention.

As shown in FIG. 3, the refractive-index measuring device 20 according to this embodiment includes a moving mechanism (light-source changing unit) 21 for moving the light source 3 between a first position $F_B$ and a second position $P_1$. The second position $P_1$ is any position away from $F_B$, as viewed from a specimen mounting surface $F_F$.

The moving mechanism 21 includes, for example, a linear moving mechanism (light-source changing unit) 22, which moves the light source 3 in the optical axis direction, and a focusing lens 23, which is retracted when the light source 3 is disposed at the first position $F_B$ and which is inserted into the light path when the light source 3 is disposed at the second position $P_1$.

With this configuration, when the light source 3 is moved to the first position $F_B$, the specimen S can be irradiated with a collimated beam. On the other hand, by moving the light source 3 to the second position $P_1$ and inserting the focusing lens (collimator lens) 23, the specimen S can be irradiated with a spot of light.

Thus, with the refractive-index measuring device 20 of this embodiment, the shape of the illumination light radiated onto the specimen S can be changed.

An apparatus moving in a straight line orthogonal to the optical axis while the distance from the optical axis is detected is omitted here.

Figure 8:
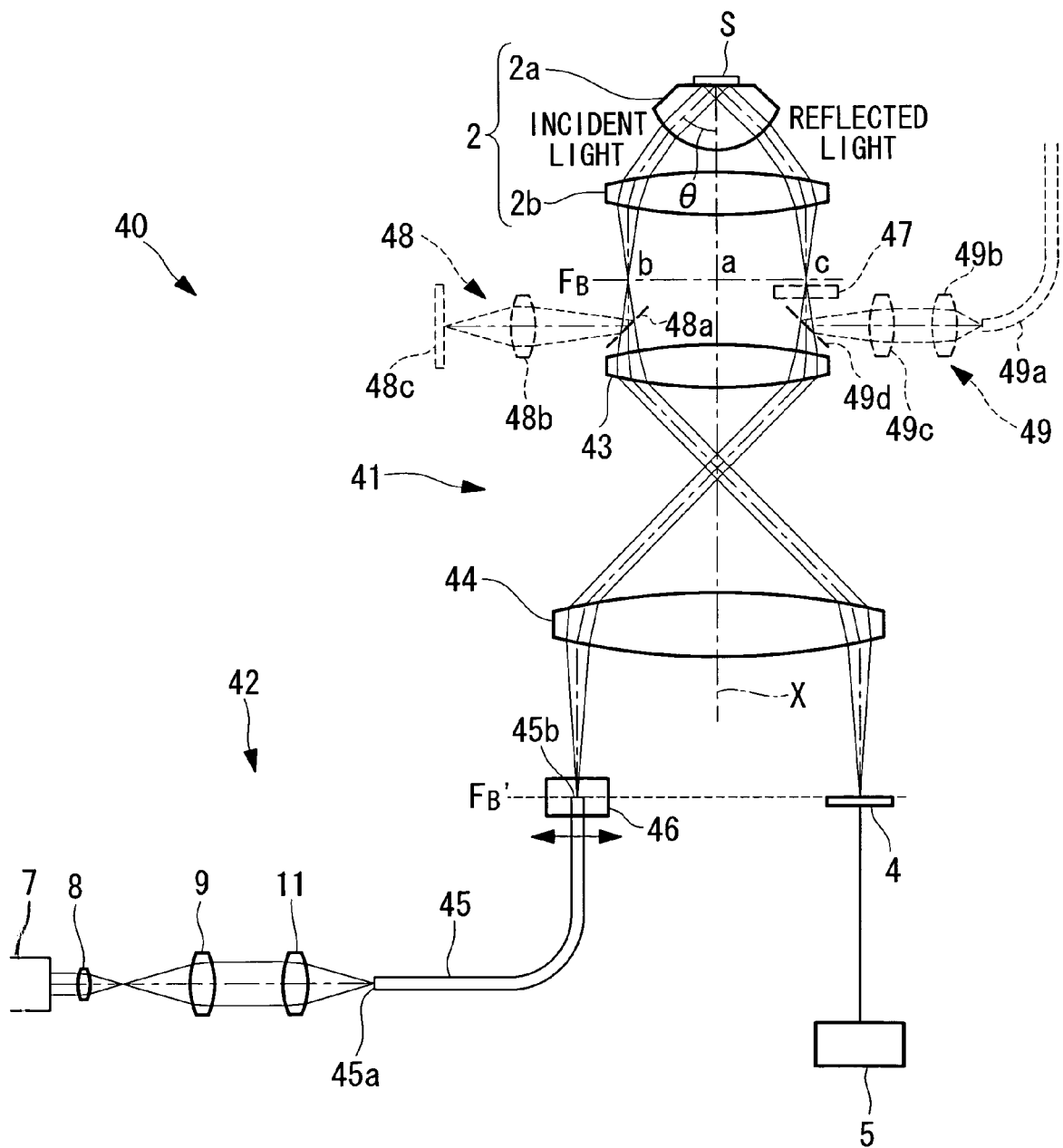
FIG. 8 is a diagram showing the overall configuration of an optical measurement apparatus according to a fourth embodiment of the present invention.

The same effect can also be obtained when an end 45b of a single-mode fiber 45, such as that shown in FIG. 8, is disposed at the position of the light source 3.

Figure 4A:
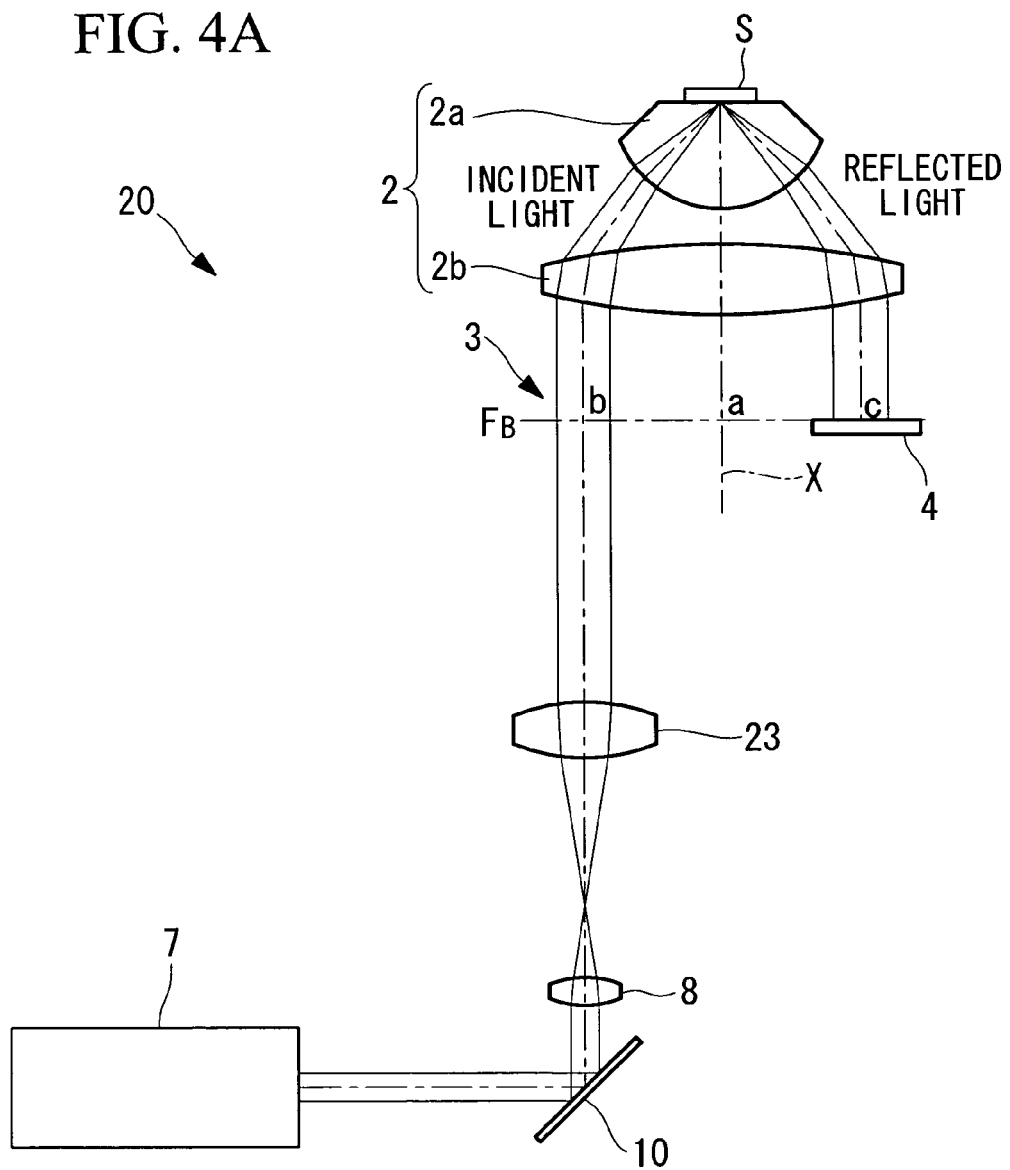
FIG. 4A is a diagram showing the overall configuration of a modification of the optical measurement apparatus in FIG. 3.
Figure 4B:
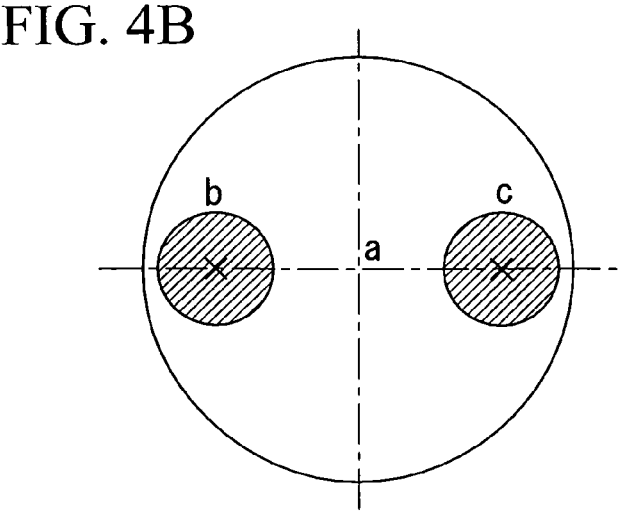
FIG. 4B is a view of a pupil plane of an optical system in the modification of the optical measurement apparatus in FIG. 3.
Figure 5A:
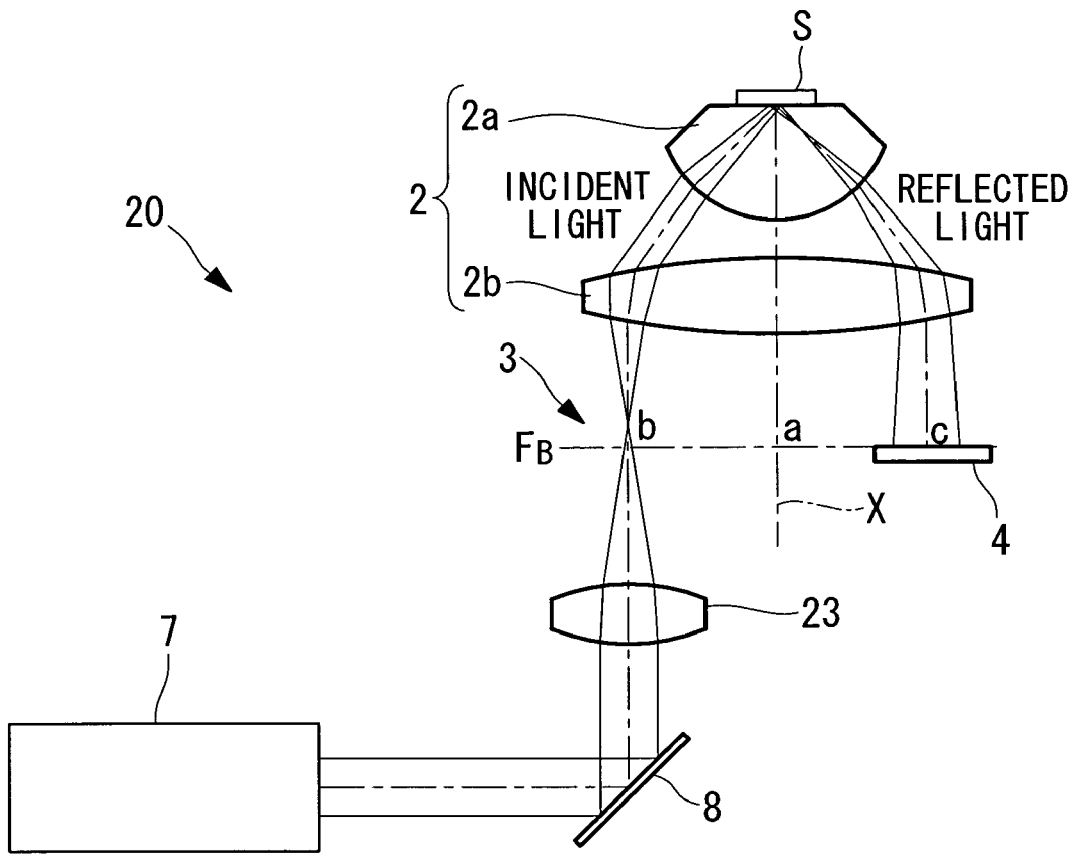
FIG. 5A is a diagram showing the overall configuration in which an optical system at a light source side is moved from the state shown in FIG. 4A.
Figure 5B:
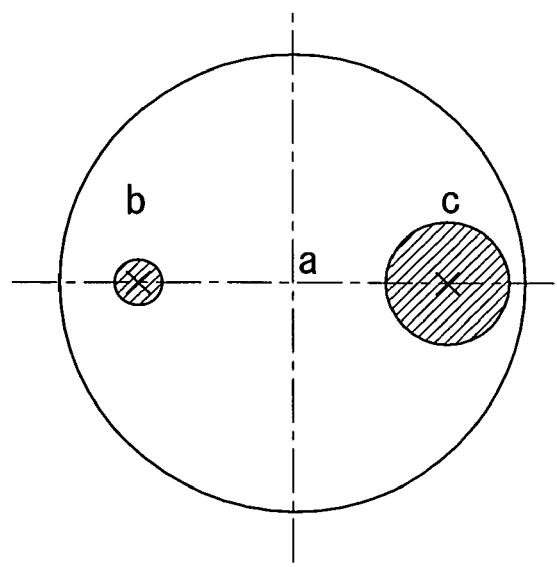
FIG. 5B is a view of the pupil plane of the optical system when the optical system at the light source side is moved from the state shown in FIG. 4A.

Also, as shown in FIGS. 4A and 5A, the light source 3 may be moved by an appropriate distance in the optical axis direction. Because a space can be ensured close to the back focal plane $F_B$, it becomes easier to install a turret, such as that shown in FIG. 6. FIGS. 4A and 4B show a collimated beam at the back focal position $F_B$ of the optical system 2. FIGS. 5A and 5B show a converging beam at position shifted from the back focal position $F_B$ of the optical system 2. In FIGS. 5A and 5B, the light reflected at the specimen S is a divergent beam that does not converge at the back focal position $F_B$ of the optical system 2. In this case, it is possible to use the approach disclosed in Japanese Unexamined Patent Application, Publication No. HEI-10-48130.

An apparatus moving in a straight line orthogonal to the optical axis while the distance from the optical axis is detected is omitted here.

An optical measurement apparatus according to a third embodiment of the present invention will be described below with reference to FIGS. 6 and 7.

In the description of this embodiment, parts having the same configuration as those in the optical measurement apparatus according to the first embodiment described above are assigned the same reference numerals, and a description thereof is omitted.

The optical measurement apparatus according to this embodiment is also a refractive-index measuring device 30.

Figure 6:
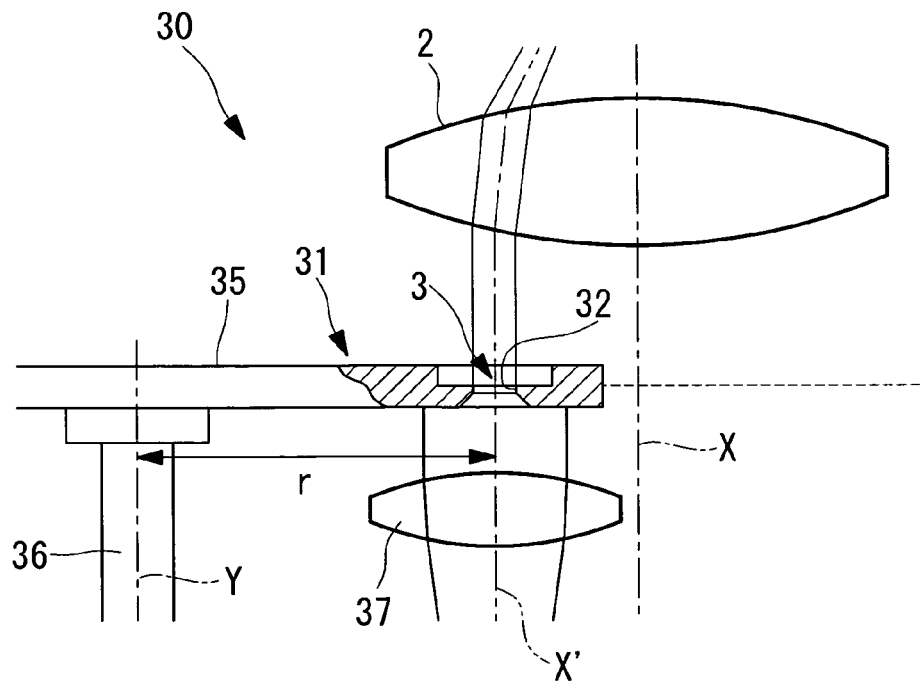
FIG. 6 is a diagram showing an optical measurement apparatus according to a third embodiment of the present invention.
Figure 7:
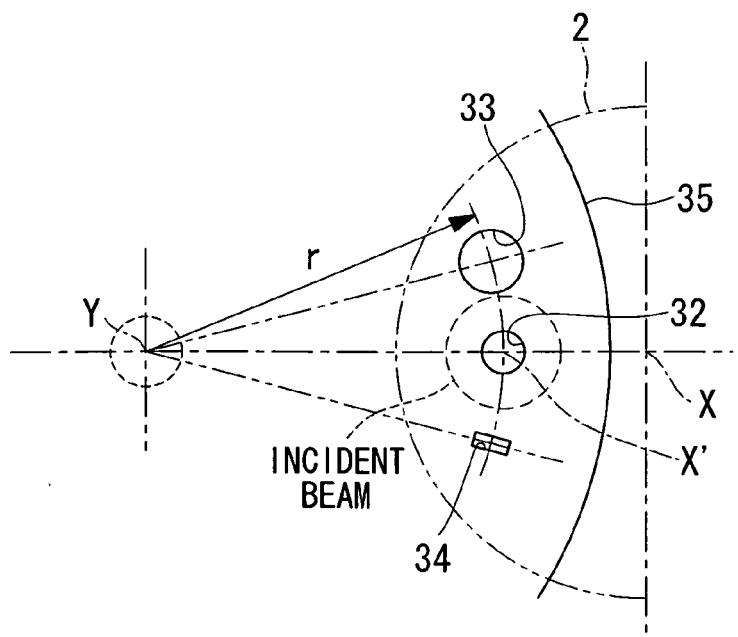
FIG. 7 is a diagram showing part of a turret in the optical measurement apparatus in FIG. 6, as viewed from the optical axis direction.

As shown in FIGS. 6 and 7, the refractive-index measuring device 30 according to this embodiment includes a diaphragm (aperture diaphragm: light-source changing unit) 31 located at the back focal position $F_B$ of the optical system 2 or at a conjugate position thereof.

FIG. 6 is a diagram showing, in outline, the configuration of the diaphragm 31 of the refractive-index measurement apparatus 30 according to this embodiment, and FIG. 7 is a view of the diaphragm 31 taken from the optical axis direction.

As shown in FIG. 7, the diaphragm 31 includes circular apertures 32 and 33 and a rectangular aperture 34. In this embodiment, the diaphragm 31 includes the first and second circular apertures 32 and 33 of different sizes. The first circular aperture 32 has a smaller opening than the second circular aperture 33.

The diaphragm 31 is provided on a circular plate-shaped turret (light-source changing unit) 35. A rod-like shaft member 36 is provided at the center of the turret 35. The turret 35 is provided at one end of the shaft member 36, and a rotary mechanism (not shown) is provided at the other end thereof. By operating this rotary mechanism, the shaft member 36 rotates about a rotational axis Y. The turret 35 may be attached to the light-source changing unit 15 shown in FIG. 1 and may be moved in a direction orthogonal to the optical axis by the moving mechanism 16.

A light-source-side optical system 37 is disposed on the opposite side of the turret 35 from the optical system 2. The rotational axis Y is parallel to the optical axis X of the optical system. The rotational axis Y is separated from an optical axis X' of the light-source-side optical system 37 by a prescribed distance r. The centers of the apertures 32 to 34 are also separated from the center of the turret 35 by distance r.

In other words, the first circular aperture 32, the second circular aperture 33, and the rectangular aperture 34 are all disposed on a circle of radius r centered at the center of the turret 35. Therefore, by rotating the turret 35, one of the first circular aperture 32, the second circular aperture 33, and the rectangular aperture 34 is disposed in the light path (optical axis X') of the light-source-side optical system 37.

A beam of prescribed diameter is introduced into the light path of the light-source-side optical system 37. The diameter of this beam is basically larger than the apertures 32 to 34 of the diaphragm 31. Therefore, upon passing through the diaphragm 31, a beam shaped to have the same shape as one of the apertures 32 to 34 is introduced into the optical system 2.

With the refractive-index measuring device 30 according to this embodiment, it is possible to change the irradiation angle of the illumination light irradiating the specimen S. Therefore, it is possible to change the spot diameter or measurement angle range on the specimen. By using a rectangular slit, it is possible to eliminate light at unwanted angles.

Next, an optical measurement apparatus according to a fourth embodiment of the present invention will be described below with reference to FIG. 8.

In the description of this embodiment, parts having the same configuration as those in the optical measurement apparatus according to the first embodiment described above are assigned the same reference numerals, and a description thereof is omitted.

The optical measurement apparatus of this embodiment is also a refractive-index measuring device 40.

As shown in FIG. 8, the refractive-index measuring device 40 according to this embodiment includes a telecentric optical system 41 and a light-source-side optical system 42 both on the opposite side of the back focal position $F_B$ from the optical system 2.

The telecentric optical system 41 includes two lenses 43 and 44 that are separated from each other in the optical axis direction.

The lens 43 is disposed so that the front focal position thereof is coincident with the back focal position $F_B$ of the optical system 2. The lens 44 is disposed so that the front focal position thereof is coincident with the back focal position of the lens 43.

The light-source-side optical system 42 includes a laser light source 7, focusing lenses 8 and 11, a collimator lens 9, and a single-mode fiber 45. One end 45a of the single-mode fiber 45 is disposed at the focal point of the focusing lens 11.

Another end 45b of the single-mode fiber 45 is disposed so as to be coincident with a back focal position $F_B'$ of the lens 44 and can be moved in a direction orthogonal to the optical axis X with a moving mechanism 46, while remaining at the back focal position $F_B'$.

The light detector 4 is also disposed at the back focal position $F_B'$ of the lens 44. In addition, it is desirable to configure the light detector 4 to be movable in the opposite direction from the end 45b of the optical fiber 45 with a moving mechanism (not shown).

In the telecentric optical system 41, the relationship f1<f2 holds, where f1 is the focal length of the lens 43, and f2 is the focal length of the lens 44. As described above, the back focal position $F_B$ of the optical system 2 is the pupil position of the optical system 2. Therefore, because the relationship f1<f2 holds in the telecentric optical system 41, an image of the pupil of the optical system 2 is formed as a magnified image at the back focal position $F_B'$ of the lens 44.

Advantages of the telecentric optical system 41 include the ability to move the light source 3 and the light detector 4 in a straight line because the measurement light and the light incident on the pupil plane and the conjugate plane thereof are perpendicular to the pupil plane, and the superior light-reception efficiency of the measurement light at right angles to the light detector 4.

Because the refractive-index measuring device 40 according to this embodiment includes the image-magnifying telecentric optical system 41, when the other end 45b of the single-mode fiber 45 is moved by the moving mechanism 46, it is possible to more precisely detect the angle θ of the beam incident on the specimen relative to the optical axis X. As a result, it is possible to measure the refractive index with higher precision.

As shown by the broken line, a polarizing element 47 may be disposed in the light path. By doing so, when the oscillating direction (polarization direction) of the laser light is disturbed by the lenses 43 and 44, it is possible to eliminate the effect of such disturbance.

In this embodiment, a common telecentric optical system 41 is used at both the light source 3 side and at the light detector 4 side. Instead of this, however, separate optical systems 48 and 49 may be disposed in the individual light paths at the light source 3 side and at the light detector 4 side, for example, as shown by the broken lines. For instance, the optical system 48 includes a mirror 48a, a focusing lens 48b, and an image sensor 48c. The optical system 49 includes, for example, a single-mode fiber 49a, a collimator lens 49b, a focusing lens 49c, and a mirror 49d. The separate optical systems 48 and 49 need not be telecentric optical systems. With the separate optical system 48 at the light-source 3 side and the separate optical system 49 at the light detector 4 side, the magnification of the optical systems may be different. Therefore, it is possible to freely change the mechanical configuration of the apparatus.

Next, an optical measurement apparatus according to a fifth embodiment of the present invention will be described below with reference to FIGS. 9 and 10.

In the description of this embodiment, parts having the same configuration as those in the optical measurement apparatus according to the first embodiment described above are assigned the same reference numerals, and a description thereof is omitted.

The optical measurement apparatus according to this embodiment is also a refractive-index measuring device 50.

Figure 9:
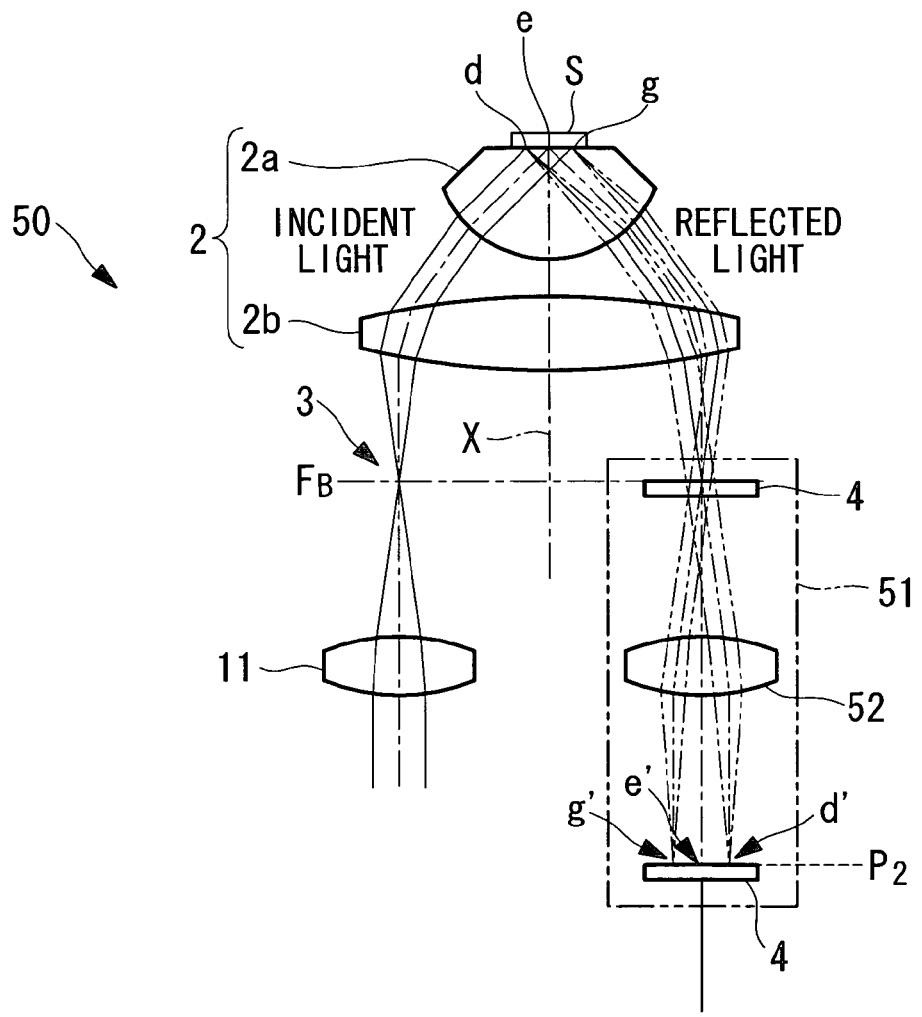
FIG. 9 is a diagram showing the overall configuration of an optical measurement apparatus according to a fifth embodiment of the present invention.

As shown in FIG. 9, in the refractive-index measuring device 50 according to this embodiment, the light detector 4 is capable of moving between a first position $F_B$ and a second position $P_2$. The first position $F_B$ is the back focal position $F_B$ of the optical system 2 or a conjugate position thereof. The second position $P_2$ is a conjugate position of the plane where the specimen S is mounted, with the measurement optical system 2 and the lens 52 disposed therebetween.

The refractive-index measuring device 50 has a moving mechanism 51 for moving the light detector 4. The moving mechanism 51 includes a lens 52 which is retracted from the light path when the light detector 4 is placed at the first position $F_B$, and which is inserted in the light path when the light detector 4 is placed at the second position $P_2$.

With the refractive-index measuring device 50 according to this embodiment, configured as described above, it is possible to measure the refractive index of the specimen S with the light detector 4 placed at the first position $F_B$. On the other hand, it is possible to observe the specimen S with the light detector 4 placed at the second position $P_2$.

Although the image of the specimen formed in the optical system at this time is half rotated, the shape of the specimen is similar. In other words, if the specimen is circular, it is possible to observe a circular image. Naturally, an image sensor is used as the light detector in this configuration. Accordingly, it is not necessary to use an image correcting means such as that disclosed in Japanese Unexamined Patent Application, Publication No. 2006-17648.

Figure 10:
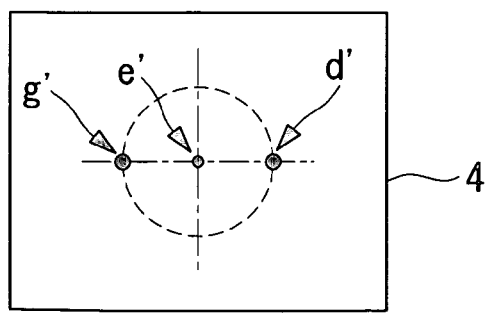
FIG. 10 is a diagram showing the position of an image formed on a light detector in the optical measurement apparatus in FIG. 9.

When observing the specimen S, as show in FIGS. 9 and 10, a point d at the edge of the specimen S is imaged at a point d' at the edge of the light detector 4. Similarly, a point e at the center of the specimen S is imaged at a point e' at the center of the light detector 4, and a point g at another edge of the specimen S is imaged at a point g' at another edge of the light detector 4. Thus, an image of the specimen S is formed on the light detector 4.

The refractive-index measuring device 50 according to this embodiment affords an advantage in that it is possible to selectively perform refractive-index measurement of the specimen S and observation of the specimen S, that is, acquisition of a refractive-index-distribution image of the specimen S.

Figure 11:
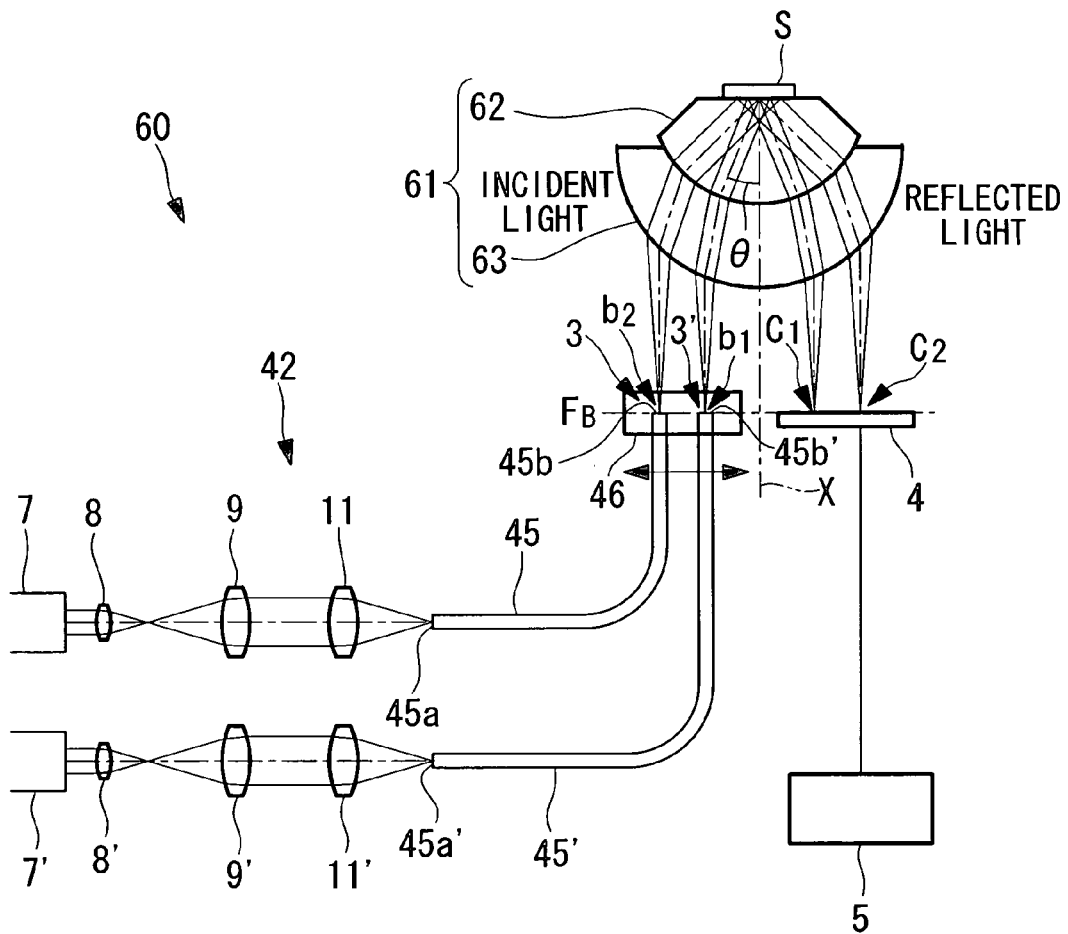
FIG. 11 is a diagram showing the overall configuration of an optical measurement apparatus according to a sixth embodiment of the present invention.

Next, an optical measurement apparatus according to a sixth embodiment of the present invention will be described below with reference to FIGS. 11 and 12.

In the description of this embodiment, parts having the same configuration as those in the optical measurement apparatus according to the first embodiment described above are assigned the same reference numerals, and a description thereof is omitted.

The optical measurement apparatus according to this embodiment is also a refractive-index measuring device 60.

The difference between the refractive-index measuring device 60 according to this embodiment and that in the first embodiment is the configuration of an optical system 61. The refractive-index measuring device 60 includes the light-source-side optical system 42 in the fourth embodiment, in which the other end 45b of the single-mode fiber 45 is disposed at the back focal position $F_B$ of the optical system 61.

The optical system 61 is formed of two lenses 62 and 63. The lens 62 has a plano-convex shape in which one surface, which is at the focal position of the optical system 61, is flat and the other surface is curved. The lens 63 has a meniscus shape in which both surfaces are curved. The lenses 62 and 63 constitute a cemented lens.

This configuration is also one example of the measurement optical system 2.

In this embodiment, the single other end 45b of the single-mode fiber 45 in FIG. 8 is moved in a direction orthogonal to the optical axis by the moving mechanism 46. Instead of this, however, as shown in FIGS. 11 and 12, a plurality of other ends 45b and 45b' of single-mode fibers 45 and 45' can be moved so as to be located at the back focal position $F_B$ of the optical system 61.

In other words, the light-source-side optical system 42 includes two laser light sources 7 and 7', two sets of focusing lenses 8, 8' and 11, 11', two collimator lenses 9 and 9', and the two single-mode fibers 45 and 45'. Although the light-source-side optical system 42 has two sets of laser light sources etc. here, it may be provided with three or more sets.

The wavelengths of the laser light emitted from the laser light source 7 and 7' are different. Fibers appropriate to the wavelengths of the guided light are selected as the single-mode fiber 45 and 45'.

Figure 12:
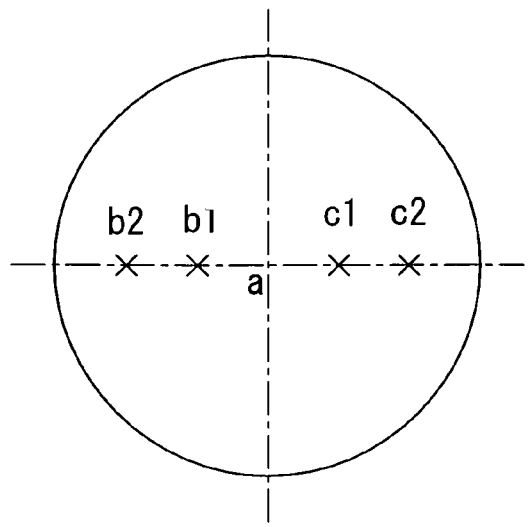
FIG. 12 is a view of a pupil plane of an optical system in the optical measurement apparatus in FIG. 11.

The back focal position $F_B$ of the optical system 61, that is, the pupil plane, is shown in FIG. 12.

In FIG. 12, the semicircular region in the left half is a space through which the incident light travels (entrance space or entrance pupil), and the semicircular region in the right half is the space through which the reflected light travels (detection space or detection pupil). Reference numeral a is the position of the optical axis X of the optical system 61. Reference numerals b1 and b2 are spot positions of the incident light. Reference numerals c1 and c2 are spot positions of the detection light.

Because the other ends 45b and 45b' of the single-mode fibers 45 and 45' are disposed at the back focal position $F_B$ of the optical system 2, this is equivalent to the two light 3 and 3' being disposed at the back focal position $F_B$ of the optical system 61. Thus, by moving the other ends 45b and 45b' in a direction orthogonal to the optical axis X with the moving mechanism 46, it is possible to measure the refractive index of the specimen S.

In this case, as shown in FIG. 12, the light spots are disposed with gaps therebetween in the direction orthogonal to the optical axis. Therefore, the angles θ formed between the collimated beams incident on the specimen and the optical axis X of the optical system 61 differ for each of the laser light sources 7 and 7'. In other words, it is possible to radiate the collimated beams onto the specimen S from inclinations at two different angles. As a result, if the wavelengths of the laser light emitted from the laser light sources 7 and 7' are different, it is possible, at the same time, to perform refractive index measurement by means of total reflection at different wavelengths while turning the light source 3 on and off by using a built-in shutter in the laser light source (not shown in the drawings). Additionally, an advantage is afforded in that it is possible to perform simultaneous measurement of not only refractive index, but also dispersion.

Figure 13:
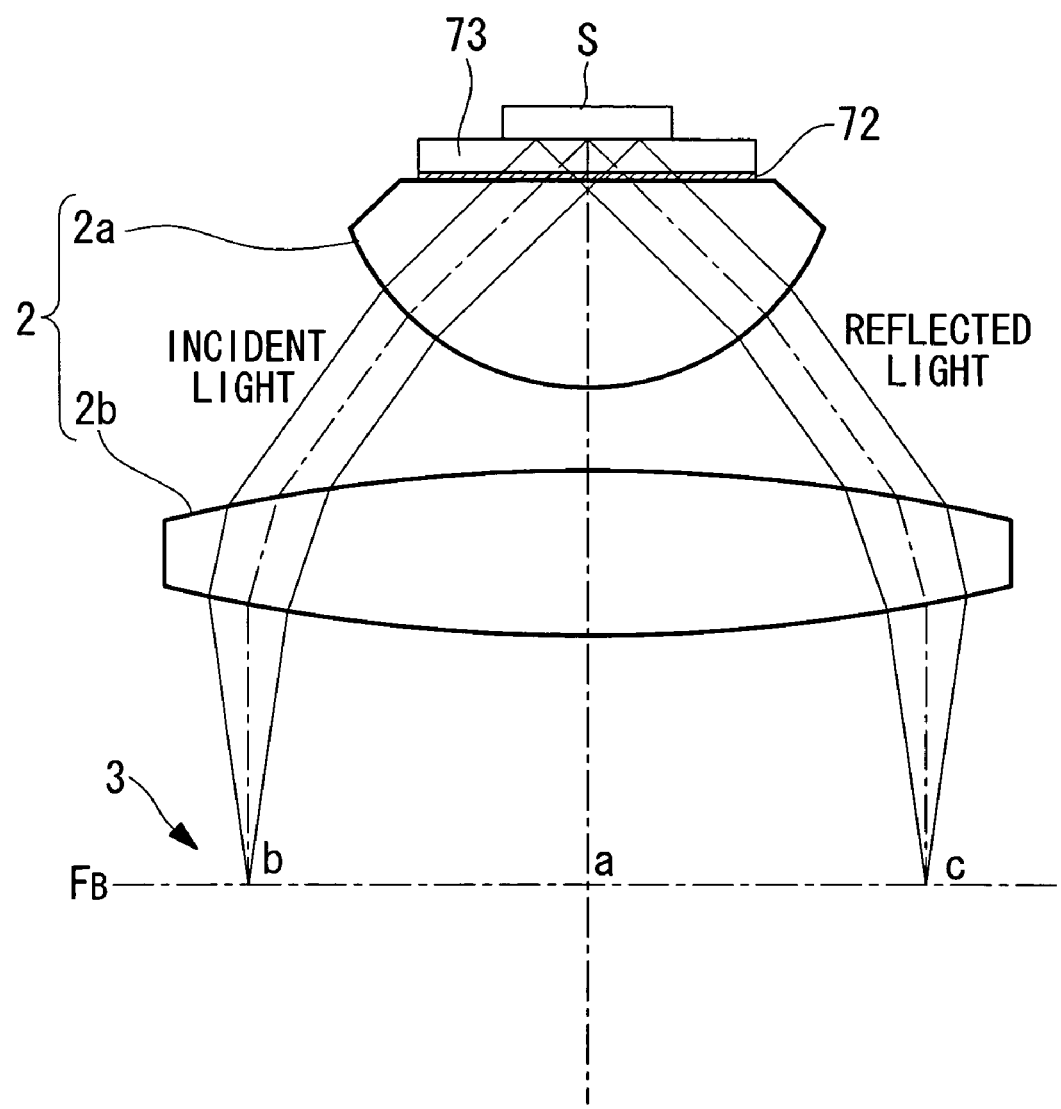
FIG. 13 is a diagram showing another modification of the optical system in the optical measurement apparatus in FIG. 1.

In each of the embodiments described above, the plano-convex lens 2a is employed as the optical element for mounting the specimen S. Instead of this, however, as shown in FIG. 13, it is possible to divide the optical member (optical element) 2a, serving as the specimen mounting stage of the measurement optical system 2, into a flat plate and a plano-convex lens, to mount a parallel flat plate (optical element) 73 on the flat surface of the plano-convex lens with a thin layer of immersion oil (liquid) 72 having substantially the same refractive index as the optical member 2a disposed therebetween, and to mount the specimen S on the parallel flat plate 73.

By doing so, because the parallel flat plate 73 can be freely removed and replaced with another one, it is possible to use parallel flat plates 73 with various optical characteristics (refractive index, etc.). In addition, the parallel flat plate 73 can be replaced if it is damaged, thus facilitating maintenance. This feature is also convenient when using the apparatus as a surface-plasmon-resonance angle measurement apparatus, wherein a thin film formed of gold etc. is formed on the flat plate. In other words, it is possible to alternately use flat plates on which thin films of various metals, including gold, are formed.

Because of the superior lubricating properties of the immersion oil, the parallel flat plate 73 disposed on the lens 2a may be moved over the flat surface of the lens 2a.

Figure 14:
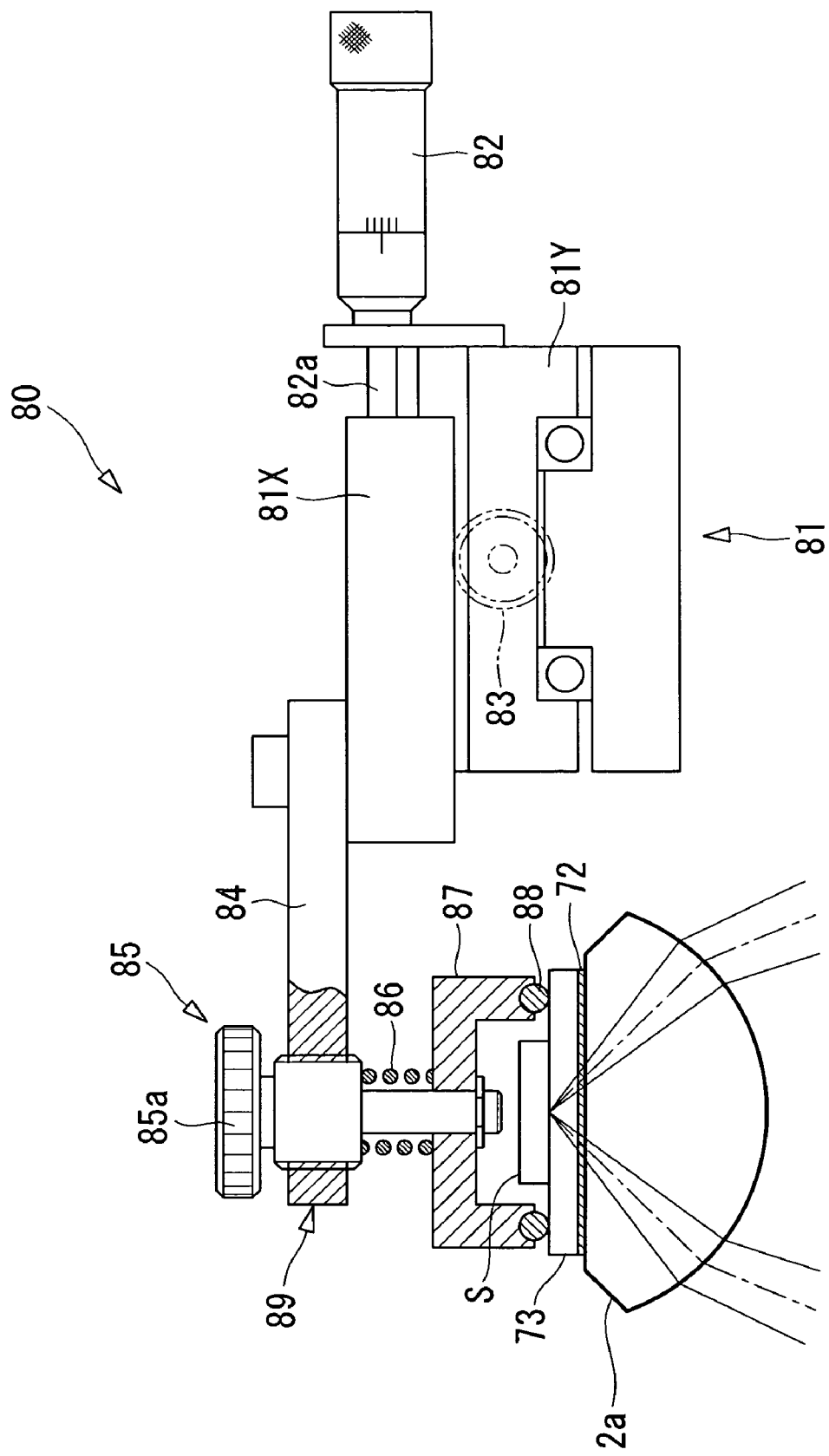
FIG. 14 is a diagram showing an example of a mechanism for moving a parallel flat plate in the optical measurement apparatus in FIG. 13.

It is possible to employ the structure shown in FIG. 14, for example, as a moving mechanism 80 for moving the parallel flat plate 73.

The moving mechanism 80 includes a two-axis stage (moving stage) 81, micrometers 82 and 83, a support arm 84, a rotating screw 85, a coil spring 86, a locking member 87, and an O-ring 88.

The two-axis stage 81 includes an X-axis stage (moving stage) 81X and a Y-axis stage (moving stage) 81Y. A head portion 82a of the micrometer 82 is connected to one end of the X-axis stage 81X.

When the micrometer (movement-amount measuring device) 82 is driven, the head portion 82a is advanced and retracted in the axial direction of the X-axis stage 81X. Therefore, it is possible to move the X-axis stage 81X. Similarly, a head portion of the micrometer 83 is connected to one end of the Y-axis stage 81Y.

The support arm 84 is mounted to the other end of the X-axis stage 81X. A holding part 89 is provided at the other end of the support arm 84. The holding part 89 holds the rotating screw 85 in such a manner as to allow it to rotate. A knob 85a is provided at one end of the rotating screw 85, and the locking member 87 is connected to the other end thereof.

The locking member 87 has a cylindrical end portion, and the O-ring 88 is disposed on this end portion. This O-ring 88 is arranged so as to make contact with the parallel flat plate 73. The coil spring 86 is held between the locking member 87 and the holding part 89 so that the O-ring 88 is pressed against the surface of the parallel flat plate 73 by the urging force of the coil spring 86.

The operation of the thus-configured moving mechanism 80 will now be described.

When the micrometers 82 and 83 are driven, the X-axis stage 81X and the Y-axis stage 81Y move. The driving force thereof is transmitted to the locking member 87 via the support arm 84. As described above, the O-ring 88 is provided at the end portion of the locking member 87, and this O-ring 88 is pressed against the parallel flat plate 73 by the urging force of the coil spring 86. Therefore, the driving force transmitted to the locking member 87 is transmitted to the parallel flat plate 73 due to the friction force between the parallel flat plate 73 and the O-ring 88.

A thin layer of the immersion oil 72 is interposed between the parallel flat plate 73 and the surface of the lens 2a. Therefore, the parallel flat plate 73 is moved relative to the lens 2a. Because the specimen S is mounted on the parallel flat plate 73, the specimen S also moves. On the other hand, because the lens 2a is fixed in position, the irradiation position of the illumination light does not change. As a result, the position of the specimen S changes relative to the irradiation position of the illumination light, and it is thus possible to irradiate different positions on the specimen S with the illumination light.

By rotating the knob 85a of the rotating screw 85, it is possible to change the position of the O-ring 88 in the optical axis X direction relative to the parallel flat plate 73. In other words, it is possible to adjust the contact force of the O-ring 88 with respect to the parallel flat plate 73.

Figure 15:
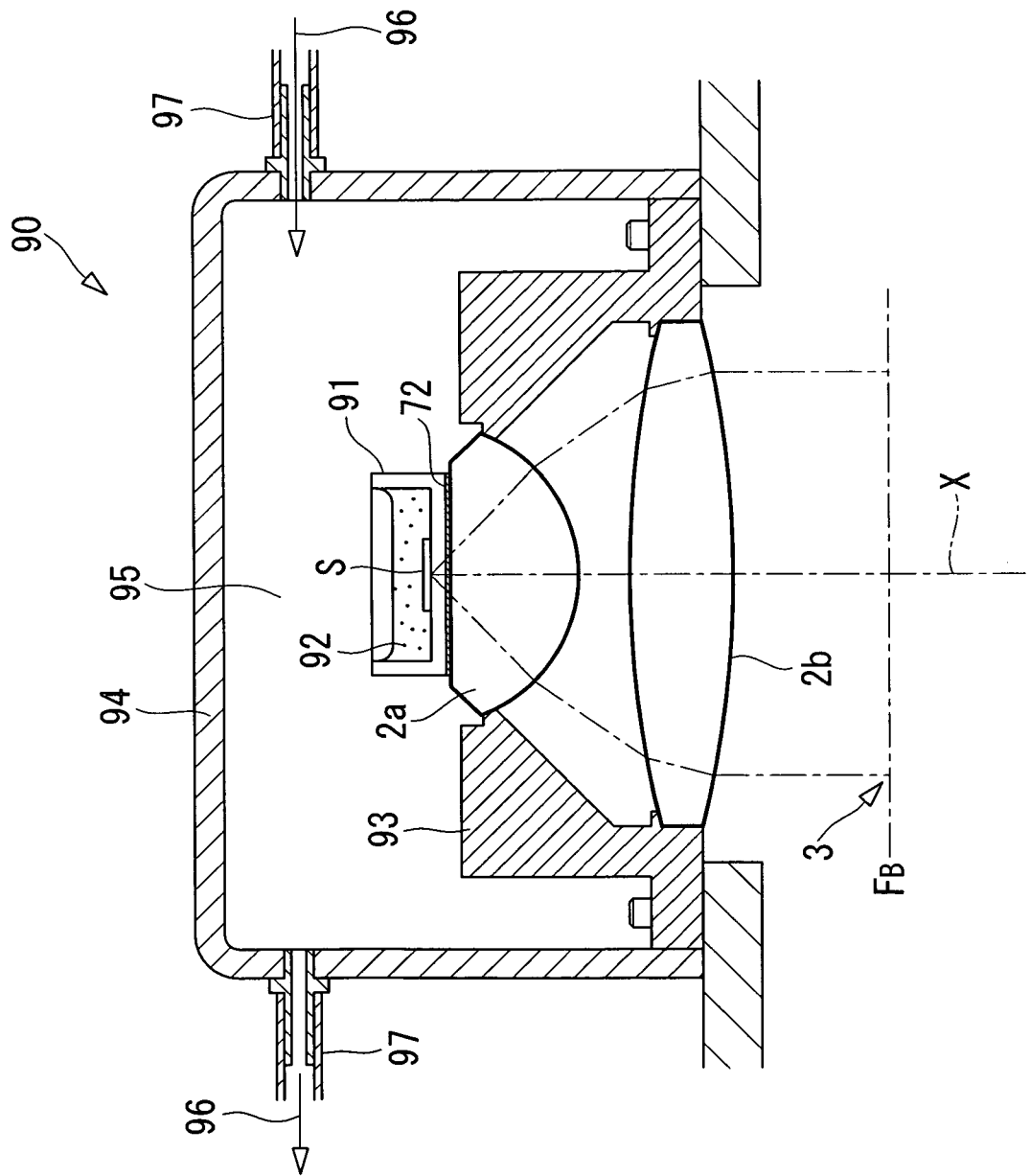
FIG. 15 is a diagram for explaining an example in which the optical measurement apparatuses in FIGS. 1 to 14 are applied to an incubator.

The refractive-index measuring devices 1, 20, 30, 40, 50, and 60 according to the embodiments described above can be applied to measurement of the refractive index of a biological specimen S in an incubator 90 shown in FIG. 15.

Instead of the parallel flat plate 73, a flat plate-shaped Petri dish 91 whose bottom surface has a prescribed thickness should be mounted on the flat surface of the lens 2a, with a thin layer of the immersion oil 72 therebetween, and the biological specimen S should be fixed to the bottom surface of the Petri dish 91, which contains a culture medium 92. An incubation space 95, which is sealed by a lens frame 93 and a sealed box 94, is formed around the Petri dish 91, and air 96 with, for example, a temperature of 37° C., a humidity of 100%, and a $CO_2$ concentration of 5% is introduced into the incubation space 95 via a tube 97. By doing so, it is possible to measure the optical characteristics, such as the refractive index, while culturing the biological specimen under suitable culture conditions.

Next, an optical measurement apparatus according to a seventh embodiment of the present invention will be described below with reference to FIG. 16.

In the description of this embodiment, parts having the same configuration as those in the optical measurement apparatus according to the first embodiment described above are assigned the same reference numerals, and a description thereof is omitted.

The optical measurement apparatus according to this embodiment is also a refractive-index measuring device 100.

The difference between the refractive-index measuring device 100 according to this embodiment and the refractive-index measuring device 1 according to the first embodiment is a light-source-side optical system 101.

The light-source-side optical system 101 includes a halogen lamp 102, a light-collecting lens 103, a pinhole 104, a collimator lens 105, a spectral device 106, a light-introducing lens 107, a multimode fiber 108, a moving mechanism 109, and a polarizing element 110.

The halogen lamp 102 is a single white light source having broad spectral properties. The polarizing element 110 may be omitted if necessary.

The halogen lamp 102 is a white light source. The light from the halogen lamp 102 is collected by the light-collecting lens 103 and passes through the pinhole 104, and is then converted to an afocal beam by the collimator lens 105 and enters the spectral device 106. In the spectral device 106, the afocal beam is split into spectral components by a grating or the like. Light of a specific wavelength is then emitted towards the light-introducing lens 107 in the form of an afocal beam and is focused at an end face of the multimode fiber 108.

The light guided in the multimode fiber 108 forms the light source 3, with a diameter equal to the diameter of the multimode fiber 108, at an end 108b disposed at the back focal position $F_B$ of the optical system 2. By doing so, it is possible to irradiate the specimen S with a substantially collimated beam from an angle.

To perform refractive-index measurement, the light source 3 at the back focal position $F_B$ of the optical system 2 should be moved in a direction orthogonal to the optical axis X by operating the moving mechanism 109.

One advantage of the refractive-index measuring device 100 according to this embodiment is the ability to easily measure the refractive index and dispersion for each wavelength, because it is provided with the spectral device 106.

The optical measurement apparatus according to this invention affords an advantage in that it is possible to switch between various measurement methods when performing optical measurement utilizing total reflection.

What is claimed is:

1. An optical measurement apparatus using total reflection, including a light source, a measurement optical system, and a light detector,
    wherein the measurement optical system is an infinity-corrected positive lens formed of an optical member having a planar surface orthogonal to an optical axis of the measurement optical system at a front focal position;
    wherein one side of the optical axis of the measurement optical system is used as a projection optical system configured to radiate measurement light onto a specimen, and another side is used as a photometric optical system configured to acquire reflected light from the specimen;
    wherein the light source is disposed at an entrance pupil position on the projection optical system side or at a position conjugate to the entrance pupil position and moves in an entrance pupil plane or in a plane conjugate to the entrance pupil position, along a straight line orthogonal to the optical axis, while a distance from the optical axis is detected; and
    wherein the light detector is disposed at an exit pupil position on the photometric optical system side or at a position conjugate to the exit pupil position;
    the optical-measurement apparatus comprising a light-source changing unit configured to change the position or shape of the light source.

2. An optical measurement apparatus according to claim 1, wherein the light source is a point light source formed by converging a collimated light beam with a focusing lens.

3. An optical measurement apparatus according to claim 1, wherein the light source is a point light source formed by guiding light with a single-mode fiber.

4. An optical measurement apparatus according to claim 1, wherein the light source is changed to a line light source orthogonal to the optical axis, which is converged by a cylindrical lens constituting the light-source changing unit, or to a line light source orthogonal to said line light source.

5. An optical measurement apparatus according to claim 1, wherein the light source is changed to a planar light source formed as a collimated beam parallel to the optical axis by an aperture member constituting the light-source changing unit.

6. An optical measurement apparatus according to claim 5, wherein the light-source changing unit includes the aperture member disposed at the entrance pupil position or at a position conjugate to the entrance pupil position.

7. An optical measurement apparatus according to claim 6, wherein the light-source changing unit moves the aperture member in a direction orthogonal to the optical axis.

8. An optical measurement apparatus according to claim 5, wherein the light-source changing unit includes a positive lens disposed in such a manner as to be insertable in and removable from the collimated beam and configured to form a point image at the entrance pupil position.

9. An optical measurement apparatus according to claim 1, wherein the positive lens is disposed behind the back focal plane of the photometric optical system, the light detector is disposed at a conjugate position, formed by the positive lens and the photometric optical system, with respect to a specimen mounting surface, and a specimen image or a refractive-index-distribution image can be observed.

10. An optical measurement apparatus according to claim 1, further comprising a white light source and a spectral device disposed at an entrance side of the light source, wherein the light source is guided by a multimode fiber.

11. An optical measurement apparatus according to claim 1, wherein the optical member comprises two optical elements, including a parallel flat plate disposed at the flat surface side, and a thin layer of liquid interposed between the two optical elements, and the parallel flat plate is disposed so as to be movable in a direction along the surface of the other optical element.

12. An optical measurement apparatus according to claim 11, wherein
    the parallel flat plate can move in a direction orthogonal to the optical axis, and
    the optical measurement apparatus further comprises a movement-amount measuring device configured to measure an amount of movement of the parallel flat plate.

13. An optical measurement apparatus according to claim 12, further comprising:
    a one-axis or two-axis moving stage configured to move the parallel flat plate,
    wherein the movement-amount measuring device is a micrometer.

* * * * *